United States Patent [19]

Jervis et al.

[11] Patent Number: 5,527,323

[45] Date of Patent: Jun. 18, 1996

[54] SURGICAL INSTRUMENT FOR TYING A KNOT IN A LENGTH OF SUTURE AT A REMOTE LOCATION

[75] Inventors: James E. Jervis, Atherton; Kenneth H. Mollenauer, Santa Clara; Karl Van Dyk, Fremont; George D. Hermann, Los Gatos, all of Calif.; Roger A. de la Torre, St. Louis; James S. Scott, St. Charles, both of Mo.

[73] Assignee: General Surgical Innovations, Inc., Portola Valley, Calif.

[21] Appl. No.: 277,987

[22] Filed: Jul. 20, 1994

Related U.S. Application Data

[63] Continuation-in-part of Ser. No. 71,297, Jun. 2, 1993, Pat. No. 5,391,176.

[51] Int. Cl.⁶ .................................................. A61B 17/00
[52] U.S. Cl. ........................... 606/148; 606/139; 112/169
[58] Field of Search ........................... 606/139, 144, 606/145, 147, 148, 151, 140, 141, 205–208; 289/17; 112/80.03, 169

[56] References Cited

U.S. PATENT DOCUMENTS

| | | |
|---|---|---|
| 1,400,653 | 12/1921 | Barbour . |
| 2,012,776 | 8/1935 | Roeder . |
| 2,566,625 | 9/1951 | Nagelmann . |
| 2,595,086 | 4/1952 | Larzelere . |
| 3,856,018 | 12/1974 | Perisse et al. . |
| 3,985,138 | 10/1976 | Jarvik . |
| 4,462,395 | 3/1983 | Johnson . |
| 4,602,635 | 7/1986 | Mulhollan et al. . |
| 4,641,652 | 2/1987 | Hutterer et al. . |
| 4,961,741 | 10/1990 | Hayhurst . |
| 5,071,412 | 12/1991 | Noda . |
| 5,084,058 | 1/1992 | Li . |
| 5,087,263 | 2/1992 | Li . |
| 5,129,912 | 7/1992 | Noda et al. . |
| 5,133,723 | 7/1992 | Li et al. . |
| 5,163,946 | 11/1992 | Li . |
| 5,201,744 | 4/1993 | Jones . |
| 5,211,650 | 5/1993 | Noda . |
| 5,217,470 | 6/1993 | Weston . |
| 5,234,443 | 8/1993 | Phan . |
| 5,242,459 | 9/1993 | Buelna . |
| 5,312,423 | 5/1994 | Rosenbluth et al. . |

FOREIGN PATENT DOCUMENTS

| | | |
|---|---|---|
| 912619 | 5/1954 | Germany . |
| 280778 | 11/1927 | United Kingdom . |

*Primary Examiner*—Stephen C. Pellegrino
*Assistant Examiner*—Jeffrey A. Schmidt
*Attorney, Agent, or Firm*—Rogers, Howell & Haferkamp

[57] ABSTRACT

A surgical instrument facilitates tying of a knot in a length of suture material at a remote surgical location. The instrument is comprised of an inner rod having a length of suture wrapped over the rod in a particular pattern. A needle may be secured to a free end of the suture and the pattern of wrapping the suture on the rod enables loops of suture to move off the rod end and over the needle to form a knot in the suture. The inner rod is received in an interior bore of an outer rod for manually controlled reciprocating movement therein. The inner rod is manually retracted into the interior bore of the outer rod to cause the outer rod to move the loops of suture off the inner rod end and over the needle in forming a knot in the suture.

27 Claims, 7 Drawing Sheets

SURGICAL INSTRUMENT FOR TYING A KNOT IN A LENGTH OF SUTURE AT A REMOTE LOCATION

This application is a Continuation-In-Part application of patent application Ser. No. 08/071,297, filed Jun. 2, 1993, now U.S. Pat. No. 5,391,176.

BACKGROUND OF THE INVENTION (1) Field of the Invention

The present invention pertains to a surgical instrument for tying a knot in a length of suture at a remote location.

(2) Description of the Related Art

Various different types of instruments are known in the prior art for use in tying knots in lengths of suture material. Many of these prior art instruments have been developed with the intent to facilitate tying knots in suture material at surgical sites located in remote areas that are difficult to access. Many prior art instruments are designed for use in surgical procedures where large, deep incisions are made into the body. The instruments enable tying knots in sutures deep in the incisions. Many prior art instruments are also designed for use in laparoscopic surgical procedures where small incisions are made and the remote surgical site is accessed through cannulas or tubes. Examples of known instruments employed in tying knots in lengths of suture material are disclosed in the Nagelmann U.S. Pat. No. 2,566,625, Larzelere U.S. Pat. No. 2,595,086, Mulhollan et al. U.S. Pat. No. 4,602,635, Hayhurst U.S. Pat. No. 4,961,741, Li U.S. Pat. Nos. 5,084,058; 5,087,263; and 5,163,946; Li et al. U.S. Pat. No. 5,133,723; and Rosenbluth et al U.S. Pat. No. 5,312,423.

A common characteristic of many known surgical knot-tying instruments is that they are very complicated to operate and time consuming to set up prior to their use. Moreover, many prior art surgical knot-tying instruments are used in a procedure that involves first tying the knot in a length of suture remote from the surgical location and then moving the loose knot along the length of suture material to a position proximate to the surgical location before the knot is tightened at the surgical location.

SUMMARY OF THE INVENTION

The present invention overcomes disadvantages commonly associated with prior art surgical knot-tying instruments by providing a simplified surgical instrument for tying a knot in a length of suture proximate to a surgical site. More specifically, the surgical instrument of the present invention may be employed in either open incision or laparoscopic surgery procedures to position a needle and a length of suture material proximate to a surgical location and to form one or more stitches with the length of suture material at the surgical location, and then to tie a knot in the length of suture material at the surgical location.

A first embodiment of the instrument is basically comprised of an elongate rod having opposite first and second ends. The longitudinal length of the rod is designed to enable the first end of the rod to be inserted through a conventional, laparoscopic trocar to position the rod first end proximate to a surgical location or site within a body cavity accessible by the trocar. The second end of the rod projects from the trocar where it is grasped manually to enable manipulation of the rod first end within the body cavity. In alternate embodiments of the invention, the rod has a shortened longitudinal length and is connected to an elongate handle that enables manipulation of the rod within the body cavity through a trocar by manual manipulation of the handle. In this embodiment of the invention, the rod is detachable from the handle for its removal and disposal after use and replacement by a like rod on the handle.

A length of suture material is provided on the rod first end. The length of suture has a needle secured to its first end and the second end of the suture is secured to the second end of the rod or to the handle. The length of suture is wrapped around the first end of the rod in a pattern of loops that will produce a knot in the length of suture when the needle is passed through the loops.

In use, the first end of the rod is positioned proximate to a surgical location by inserting the rod end into an open incision or by inserting the rod first end through the interior of a trocar providing access to a body cavity. With the first end of the rod positioned proximate to the surgical location, one or more stitches are made in the desired positions at the surgical location. In preparation to form a first throw of a knot in the suture material, the needle is inserted into the rod first end beneath the first loop of suture material formed on the rod end. The needle is released by the grasper and then retaken by the grasper at the distal end of the needle projecting from beneath the first suture loop. The needle and the first end of the suture material are then pulled from beneath the first suture loop causing the first loop to move off the first end of the rod. As the needle and first end of the suture are continued to be pulled away from the rod first end, the first loop moves down the length of suture toward the stitch made at the surgical location, forming a first throw of a knot in the suture material securely closing the stitch. This procedure may be repeated as many times as there are suture loops formed on the rod first end to form a knot of any desired number of throws. When the desired knot is formed at the stitch in the surgical location the two lengths of suture extending from the knot are cut and the knot-tying instrument and needle are removed from the surgical location.

In a further embodiment of the rod it is employed as an inner rod of a knot tying instrument comprising concentric inner and outer rods. The inner rod has a length of suture wrapped around one of its ends and the opposite end is inserted into an interior bore of the second tubular rod for reciprocating movement of the first rod in the interior bore of the second rod. The proximal end of the length of suture is held by the surgeon's hand or is secured in some manner to the exterior of the instrument, for example by a clamp. The suture distal end extends from the pattern of loops on the inner rod to the needle. The first rod reciprocates in the bore of the second rod between an extended position of the first rod relative to the second rod where a portion of the exterior surface of the first rod having the length of suture wrapped thereon projects from a distal end of the second rod, to a retracted position of the first rod relative to the second rod where the first rod is completely contained inside the interior bore of the second rod. A manual handle is provided on this embodiment of the invention for retracting the first rod into the interior bore of the second rod. As the first rod is retracted into the interior bore of the second rod, the distal end of the second rod passes over the exterior surface of the first rod sliding the loops of suture wrapped on the exterior surface of the first rod off from its distal end.

In use of this embodiment, a stitch is made with the needle as in the previously described embodiments and a portion of the length of suture attached to the needle is pulled through the stitch so that the needle may be positioned adjacent the distal ends of the concentric rods. The needle is then inserted through the loops of the suture material as they are pushed off from the end of the first rod by the distal end of the second rod as the first rod is retracted into the interior bore of the second rod. The needle, with the length of suture still attached, is then pulled tight causing the loops through which the needle and suture have been inserted to move down the length of suture to the site of the stitch. By continuing to pull the end of the suture material attached to the needle and the end of the suture material attached to the rod or held by the surgeon, a knot is formed at the site of the stitch. The portions of suture extending from the knot are then cut proximate to the knot and the surgical instrument and needle are removed from the location.

BRIEF DESCRIPTION OF THE DRAWINGS

Further objects and features of the present invention are revealed in the following detailed description of the preferred embodiments of the invention and in the drawing figures wherein.

DESCRIPTION OF THE PREFERRED EMBODIMENTS

Figure 1:
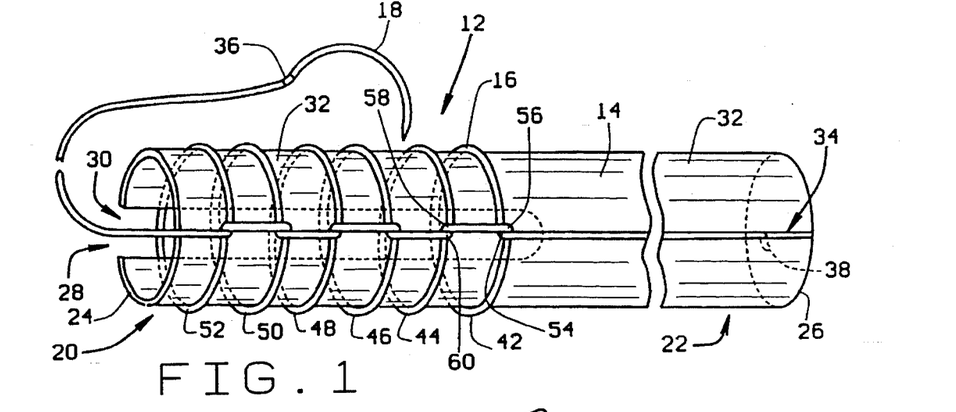
FIG. 1 shows a fragmented perspective view of the surgical instrument for tying a knot in a length of suture.
Figure 4:
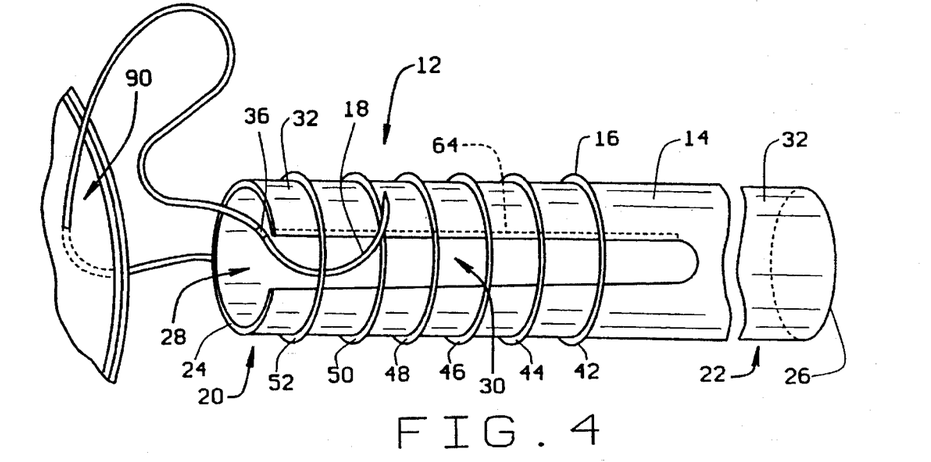
FIG. 4 shows a fragmented perspective view similar to that of FIG. 1 with the instrument of the invention rotated 180°.

A first embodiment of the surgical instrument 12 of the present invention is shown in FIGS. 1 and 4. This first to be described embodiment of the invention, as well as other embodiments of the invention yet to be described, may be constructed of any materials acceptable for use in surgical operations. The instrument is basically comprised of an elongate rod 14, a length of suture material 16 secured to the rod, and a needle 18 secured to the length of suture material.

The elongate rod has opposite first 20 and second 22 ends, or left hand and right hand ends respectively, adjacent opposite first 24 and second 26 end faces, or left and right end faces, as viewed in FIGS. 1 and 4. A hollow interior bore 28 extends longitudinally through the rod 14 between its end faces 24, 26. The interior and exterior diameter dimensions of the rod 14, as well as its longitudinal length between end faces, may vary depending on the intended application of the instrument. The instrument is designed for use with both open incision surgery and laparoscopic surgery and the rod 14 of the instrument may be dimensioned so that it can be easily inserted through the interior of a trocar in laparoscopic surgery applications. Additionally, the lateral dimensions of the instrument rod 14 may be enlarged to further facilitate its use in open incision surgical operations. The dimensions of the rod 14, suture material 16, and needle 18 shown in the drawing figures are not to scale and are not proportionate but are enlarged in FIGS. 1 and 4 to better illustrate the component parts of the invention and their relationship to each other. Moreover, it is not necessary that the instrument rod have the cylindrical configuration shown in FIGS. 1 and 4.

A slot 30 is formed through the exterior surface 32 of the rod adjacent its first end 20 forming a recess or indentation into the rod from the exterior surface to the interior bore 28. A second smaller slot 34 or slit is formed in the second end 22 of the instrument rod extending along a portion of the longitudinal length of the rod from the second end face 26.

The length of suture material 16 has opposite first 36 and second 38 ends with the first end 36 of suture material being secured to the needle 18 in a conventional manner. The total length of the suture material between its first and second ends may vary depending on the intended application of the surgical instrument of the invention, as will be explained. The second end 38 of the suture is secured adjacent the rod second end 26 by inserting the suture into the narrow slot 34. In variant embodiments of the invention, the second end 38 of the suture may be secured to the instrument rod 14 in any equivalent manner, or may be manually held adjacent the rod second end in use of the surgical instrument. The length of suture 16 extends from the instrument rod second end 22 along the exterior surface of the rod toward the rod first end 20 and is wrapped in several loops 42, 44, 46, 48, 50, 52 at the first end 20 of the rod. From the last of the plurality of loops, the suture material extends to its first end 36 secured to the needle 18.

As best seen in FIG. 1, each of the loops of suture material are wrapped around the exterior surface of the rod in a specific configuration that enables individual loops to be spaced from each other along the rod first end 20 and also enables individual loops to be manipulated to slide along the longitudinal length of the rod first end without causing adjacent loops to move along the length of the rod. Although a specific arrangement of the suture material to form the plurality of loops is shown in FIG. 1, it should be appreciated that the suture material 16 may be formed in a variety of different loop configurations on the rod first end 20 that enable the plurality of suture loops to be spaced from each other as shown in FIG. 1 and allow individual loops of suture material to be manually moved longitudinally over the exterior surface of the rod without causing adjacent loops to be moved.

The specific configuration of the suture loops shown in FIG. 1 is produced by forming a first bend 54 in the suture material 16 as it extends longitudinally over the exterior surface of the rod 14 from the second end 22 toward the first end 20 of the rod. From the first bend 54, the suture material extends laterally relative to the rod and is wrapped one complete revolution around the exterior surface of the rod back to the first bend 54. The suture material is then formed in a second bend 56 around the first bend 54 of the suture and again extends longitudinally along a portion of the rod's length, thereby completing the formation of the first loop 42 in the suture material. The subsequent or adjacent loop 44 is formed in substantially the same manner as the first described loop 42. In forming the second loop, a first bend 58 is formed in the suture material and the suture extends from the first bend laterally around the exterior surface of the rod 14 one complete revolution back to the first bend of the second loop. Next, a second bend 60 is formed in the suture material around the first bend 58 of the second loop. The suture material continues to extend longitudinally toward the rod first end 20 from the second bend 60, thereby completing the second loop 44 of suture material formed on the exterior of the rod 14. The remaining pairs of loops 46 and 48, 50 and 52, are formed in the suture material as it extends toward the rod first end 20 in the identical manner as the first pair of loops 42, 44 just described.

To illustrate that the loops of suture material formed over the exterior surface of the rod 14 may be formed in a variety of different configurations without departing from the intended scope of the claims of the invention, it is noted that the first and second loops 42, 44 are substantially mirror images of each other, and the second and third loops 44, 46 are also substantially mirror images of each other. In variations of the invention, these first three loops of suture material may have been wound around the exterior surface of the rod 14 so that their configurations are substantially identical to each other, as are the first and third loops 42, 46. Moreover, all of the loops of suture material could have been wrapped around the exterior of the rod 14 in substantially the same configuration as the first loop 42 or all of the plurality of loops could have been wrapped in substantially the same configuration as the second loop 44 without departing from the intended scope of the claimed invention and without altering the operation of the invention or its method of use.

To prevent the plurality of suture loops from unraveling from the rod first end 20 and to prevent the needle 18 from hanging free from the rod first end a strip magnet 64 is encased in the material of the rod first end extending along one side of the first slot 30 as shown in FIG. 4. By positioning the needle 18 adjacent the side of the slot 30 having the strip magnet 64, the needle is held securely in place at the rod first end 20 as shown in FIG. 4. Alternate means of securing the needle 18 at the rod first end 20 may be employed in place of the strip magnet 64.

In variant embodiments of the instrument rod 14 the strip magnet 64 could be eliminated from its position adjacent the slot 30 and the needle 18 could be held in place relative to the rod by a conventional laparoscopic surgery grasper inserted through the rod interior bore 28 from its second end 22.

Figure 2:
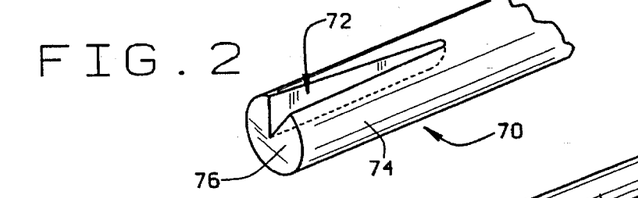
FIG. 2 shows a partial perspective view of a variant embodiment of the instrument of the invention.

FIG. 2 shows a variant embodiment of the rod 70 of the surgical instrument. In this embodiment, the rod again has a cylindrical configuration; however, the rod does not have a hollow interior bore as in the first embodiment. The rod configuration shown in FIG. 2 is solid with the slot 72 extending down into the interior of the material of the rod from the exterior surface 74. The longitudinal length of the slot 72 is determined to enable the slot to extend beneath the plurality of loops formed in suture material (not shown) wrapped over the first end of the rod 70. The remaining component parts, i.e. the suture material and needle, of the second embodiment of the surgical instrument employing the solid rod 70 are substantially identical to those of the first described embodiment of FIGS. 1 and 4.

Figure 3:
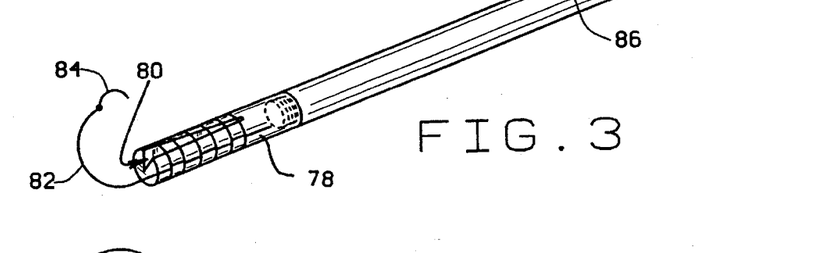
FIG. 3 shows a perspective view of a still further embodiment of the instrument of the invention.

FIG. 3 shows a still further variant embodiment of the surgical instrument rod 78. In the embodiment of the rod 78 shown in FIG. 3, the first end, or left hand end of the rod as viewed in FIG. 3, may have the same tubular configuration of the first described embodiment of FIGS. 1 and 4 or may have the solid configuration of the rod shown in FIG. 2. The rod has a slot 80 formed in its first end in the same manner as the previously described embodiments and a length of suture material is wrapped over the exterior surface of the rod and the slot with one end of the suture secured to the rod and the opposite end of the suture secured to a needle 82 in the same manner as the first described embodiments. The embodiment of FIG. 3 differs from the previously described embodiments in that the longitudinal length of the surgical instrument is divided into two sections with the first section comprising the rod 78 and the second section comprising a handle 86. As shown in FIG. 3, the second end of the rod 78 is detachably secured to one end of the handle 86 by a threaded connection 88. Other equivalent means of providing a releasable connection may also be employed. The ability of the rod 78 to be detached from the handle 86 enables the rod to be detached and disposed of after use and replaced on the handle by a like rod.

FIGS. 5–10 are schematic representations of the method of the invention employed in using the surgical instrument of the invention for tying a knot in a length of suture in a laparoscopic surgical operation. The drawing figures and their descriptions to follow only generally describe one use of the surgical instrument of the invention and are employed only to illustrate some benefits provided by the surgical instrument of the invention. Drawing FIGS. 5–10 and their descriptions to follow describe use of the surgical instrument of the invention in laparoscopic surgery forming a single stitch to close an incision. Again, it should be understood that the description to follow is illustrative only and should not be interpreted as limiting the use of the surgical instrument of the invention to only laparoscopic surgical techniques or only use in forming one stitch in securing adjacent tissues together. The benefits provided by the unique surgical instrument of the present invention suit it for use in a variety of different known surgical techniques and for use in forming both a single stitch and a line of stitching in body tissues.

Figure 5:
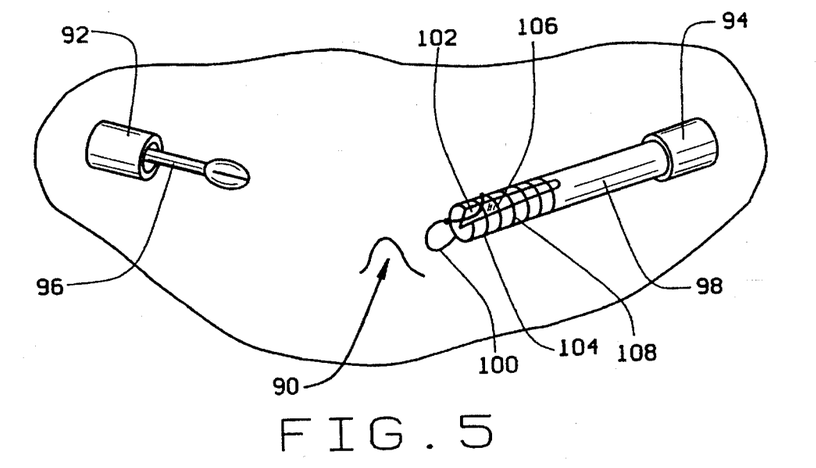
FIG. 5 is a schematic representation of a step involved in the method of use of the instrument of the invention in tying a knot in a length of suture in laparoscopic surgery.
Figure 6:
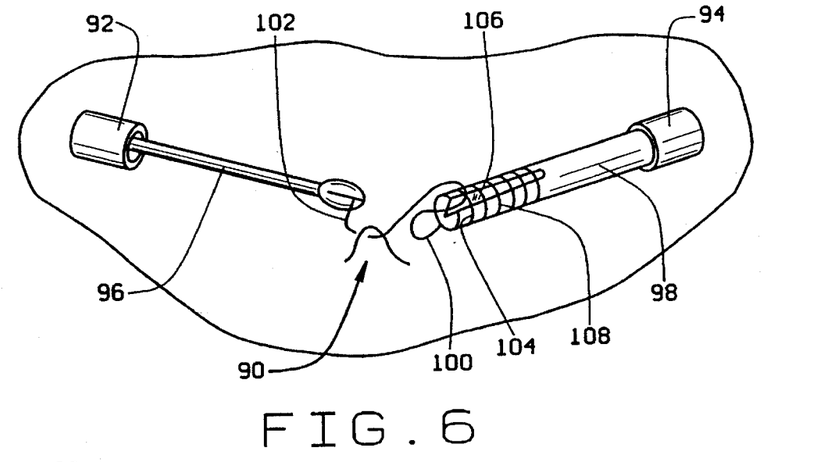
FIG. 6 is a subsequent step to that shown in FIG. 5.
Figure 7:
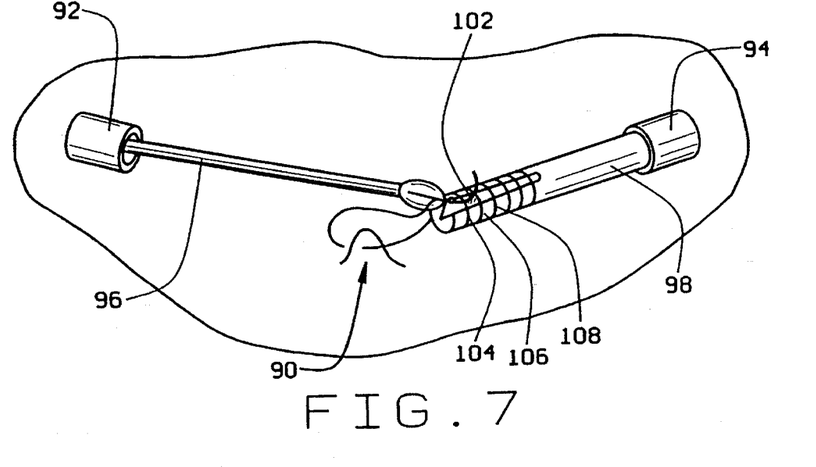
FIG. 7 is a subsequent step to that shown in FIG. 6.
Figure 8:
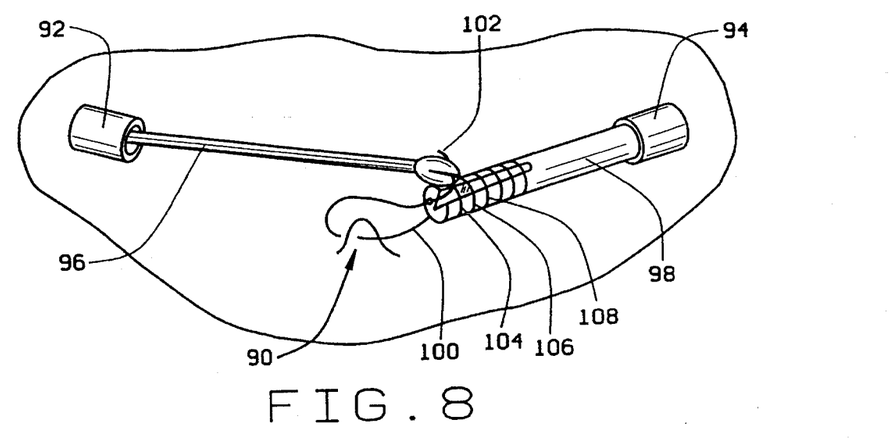
FIG. 8 is a subsequent step to that shown in FIG. 7.

FIG. 5 is a schematic representation of a view looking inside a body cavity toward an opening in a tissue 90 representing a defect to be repaired or mended by use of the surgical instrument of the invention. The drawing figure and FIGS. 6–10 to follow illustrate a laparoscopic repair of the defect 90 in the tissue and a pair of trocars 92, 94 are shown already inserted through left and right flanks of the body into the cavity, respectively. Graspers 96 are shown inserted through the left trocar 92 into the body cavity and the first end of the surgical instrument rod 98 with the length of suture 100 wrapped thereover and the needle 102 secured to the suture are shown inserted through the right trocar 94. The needle 102 is shown releasably held to the first end of the instrument rod 98 by a magnet encapsulated in the material of the rod, as was explained earlier. The length of suture extending from the needle 102 to the first suture loop 104 formed on the rod end may be longer than that shown in FIG. 5 to facilitate manipulation of the needle in producing a stitch through the defective tissue 90. The excess length of suture between the needle 102 and the first suture loop 104 may be spirally wound on the rod first end between the rod end face 106 and the first loop 104. In preparing to use the instrument of the invention, the second end of the rod 98 (not shown) extending from the exterior end of the trocar 94 is manipulated to position the rod first end proximate to the surgical location or the defective tissue 90. The graspers 96 are then used to remove the needle 102 from its magnetic attachment to the rod end and a stitch is made through the tissue defect 90 at the surgical location. Only one stitch is shown being made in FIG. 6; however, as explained earlier, the surgical instrument of the invention may be employed in forming a line of stitching to close a larger tissue defect. In forming a line of stitching, the needle and attached length of suture are passed through the tissue defect several times along the line in one direction and then are passed again through the tissue defect along a return line back to the position where the suture was first inserted through the tissue. This positions the length of suture extending to the tissue defect from the instrument rod and the length of suture extending from the tissue defect to the needle adjacent each other. With these two lengths of suture positioned adjacent each other a knot may be formed in the suture in the same manner as after forming a single stitch in the tissue defect.

Figure 9:
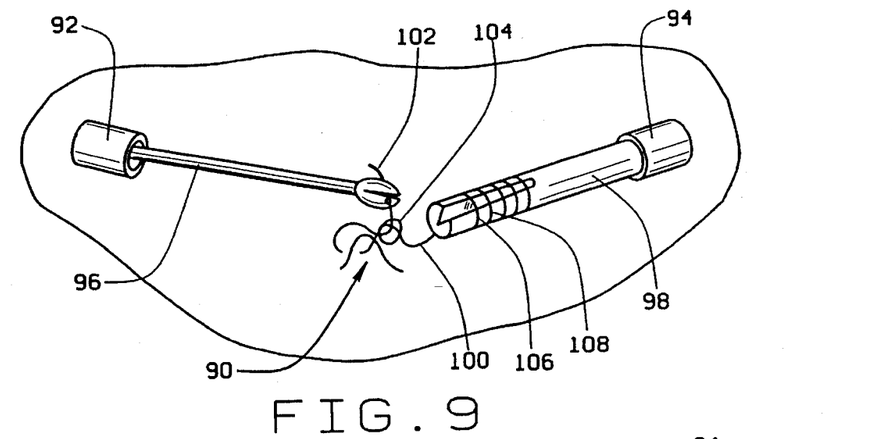
FIG. 9 is a subsequent step to that shown in FIG. 8.
Figure 10:
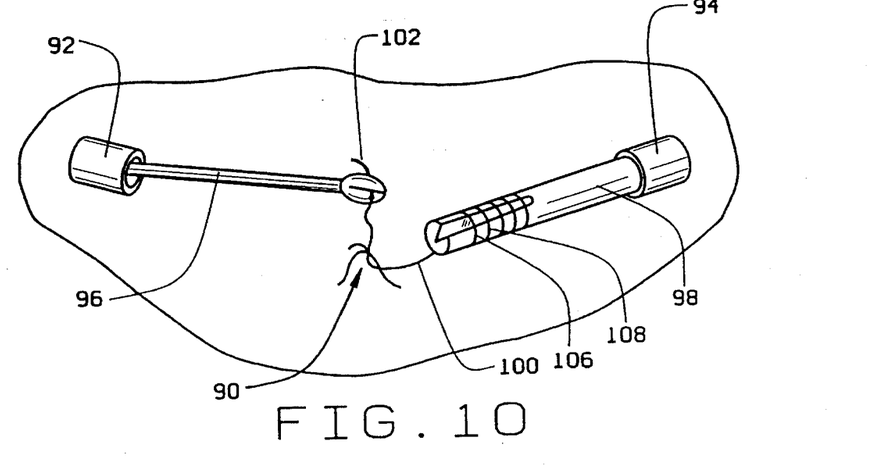
FIG. 10 is a subsequent step to that shown in FIG. 9.

In preparation to form a first throw of a knot in the suture material, the needle is repositioned by the grasper in the slot in the first rod end with the needle extending beneath the first loop 104 of suture material formed on the rod end. FIG. 4 shows in more detail the proper positioning of the needle in preparing to form the first throw of the surgical knot. The needle is held in this position beneath the first loop of the suture by the magnetism of the first rod end. The needle is then released by the grasper 96 and then retaken by the grasper at the distal end of the needle, or the point end of the needle projecting from beneath the first suture loop 104 and out of the slot as viewed in FIG. 8. The needle and attached suture material are then pulled from the instrument slot and from beneath the first suture loop 104 causing the first loop to move off of the first end of the rod as shown in FIG. 9. As the needle and first end of the suture are continued to be pulled away from the rod first end by the grasper, the first loop 104 moves down along the length of suture attached to the needle toward the stitch made at the surgical location in the tissue defect 90, forming a first throw of a knot in the suture material securely closing the stitch, as shown in FIG. 10.

The above process is repeated with the needle and attached suture passing through the slot and beneath the second loop 106 of suture formed on the exterior of the rod first end. As the needle and attached suture are pulled out of the slot and from beneath the second loop 106, the second loop is pulled off the rod first end down the length of suture attached to the needle. As the needle and attached suture are continued to be pulled away from the rod first end, the second loop arrives at the stitch formed by the first throw and forms a second throw of the knot at the stitch. If so desired, the procedure is repeated a third time by inserting the needle beneath the third loop 108 of suture and pulling the needle from beneath the loop and from the rod first end to cause the third loop to move off the rod end and down the suture forming a third throw in the knot at the stitch. This procedure may be repeated as many times as there are suture loops formed on the rod first end to form a knot of any desired number of throws. When the desired knot is formed at the stitch in the surgical location, the two lengths of suture extending from the knot are cut and the knot-tying instrument and needle are removed from the surgical location.

It should be appreciated that the surgical instrument of the invention facilitates tying a knot in a length of suture material at a remote surgical location by enabling the positioning of the suture material proximate to the surgical location and by holding the suture material at the surgical location in a manner that enables one or more throws of a knot to be easily formed in the suture material.

Figure 11:
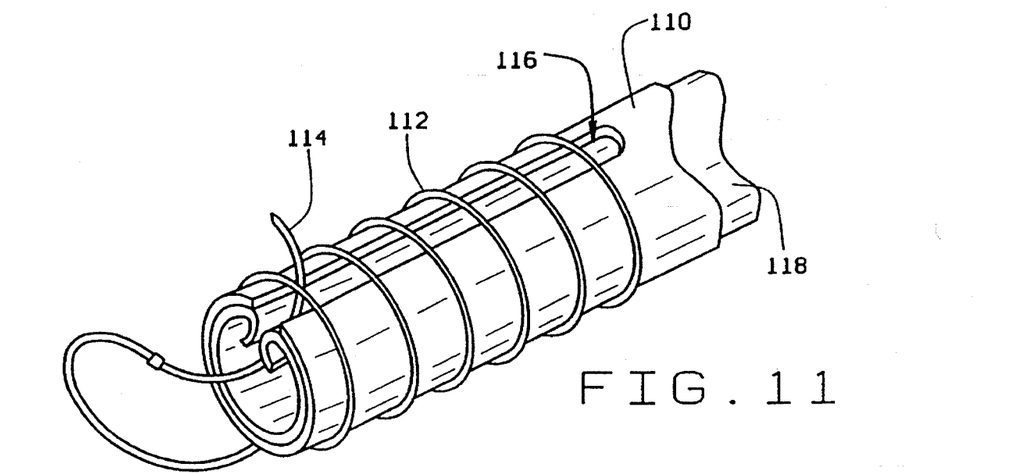
FIG. 11 shows a partial perspective view of a further embodiment of the invention.

FIG. 11 shows a still further embodiment of the rod 110 of the surgical instrument similar to the embodiment shown in FIG. 3. In this embodiment, the rod has substantially the same configuration as the embodiment shown in FIGS. 1 and 4 with the length of suture material 112 and the needle 114 affixed thereto looped over the exterior surface of the rod 110 in substantially the same manner as that described with reference to FIGS. 1 and 4. The rod 110 has a slot 116 formed in its first end in the same manner as the previously described embodiment of FIGS. 1 and 4 and the length of suture material is looped over the slot. Like the FIG. 3 embodiment, in the FIG. 11 embodiment the longitudinal length of the surgical instrument is divided into two sections, with the first section comprising the rod 110 and the second section comprising a tubular handle 118 having a first end inserted through the interior of the rod. As shown in FIG. 11, the rod 110 is detachably secured to the first end of the handle 118 by being slipfit over the end of the handle. The interior diameter of the rod 110 is substantially equal to the exterior diameter of the handle 118 so that the rod 110 may be easily slipfit over the end of the handle 118 and held on the handle end by friction engagement. The rod has a slot 120 that is equal in length to the slot 116 of the rod and is aligned with the rod slot. Like the embodiment of FIG. 3, the longitudinal length of the instrument handle 118 enables it to be used in both deep open incisions or in laparoscopic surgery as in the previously described embodiments. The ability of the rod 110 to be detached from the handle 118 enables the rod to be detached and disposed of after use and replaced on the handle by a like rod. With the configuration of the surgical instrument shown in FIGS. 11 and 12, once the length of suture has been used from one rod 110 of the instrument the used rod may be detached from the handle 118 and replaced with a new rod having a length of suture looped over its exterior surface.

Figure 12:
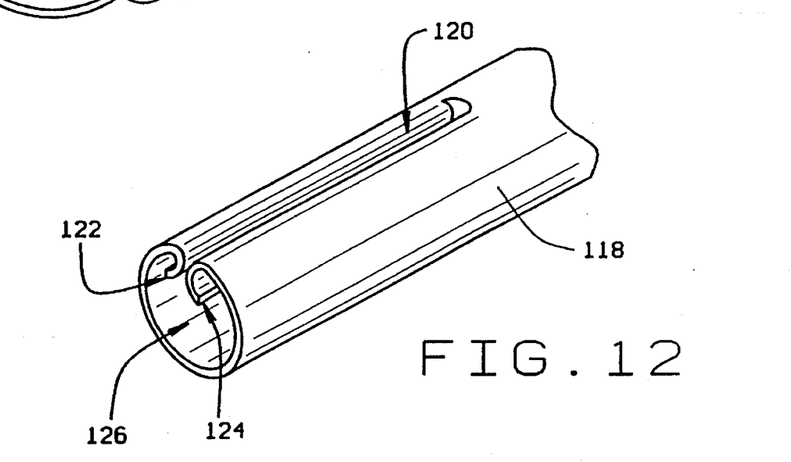
FIG. 12 shows a partial perspective view of a handle used with the embodiment of FIG. 11.

As explained above, the handle slot 120 has a longitudinal length substantially equal to that of the rod slot 116 but is also provided in a specific configuration that enables the handle slot 120 to grip the needle 114 between the opposite lateral edges of the slot. With the handle slot 120 having such an ability, it is no longer necessary to provide a magnetic strip along the slot of the rod 110 to temporarily hold the needle 114 while using the instrument of the invention. As best seen in FIG. 12, the opposite lateral ends 122, 124 of the handle slot 120 are curved underneath and then back toward the interior surface of the handle 118. This gives the handle slot 120 a much narrower width than the slot 116 of the rod 110 enabling it to pinch grip the needle 114 within the slot.

Figure 13:
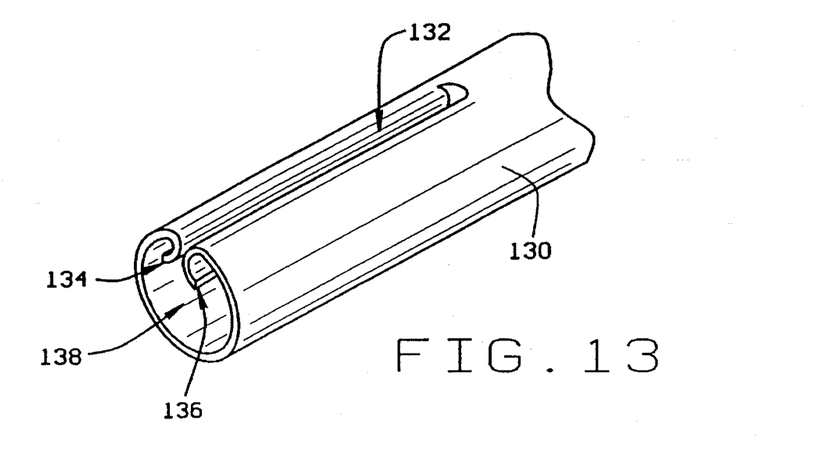
FIG. 13 shows a partial perspective view of a further embodiment of the invention.

A still further embodiment of the rod 130 of the surgical instrument of the invention is shown in FIG. 13. This embodiment of the rod 130 is substantially identical to the first described embodiment of FIGS. 1 and 4 except for the configuration of the rod slot 132. The first end of the rod 130 has the same cylindrical configuration of the first described embodiment of FIGS. 1 and 4 and although not shown, a length of suture material is wrapped over the exterior surface of the rod and the slot 132 with one end of the suture secured to the rod and the opposite end of the suture secured a needle in the same manner as the first described embodiment. The embodiment of FIG. 13 differs from the previously described embodiment of FIGS. 1 and 4 in that the configuration of the slot 132 is substantially identical to that of the just described embodiment of the instrument handle 118 shown in FIGS. 11 and 12.

FIGS. 14–17 show a still further embodiment of the surgical instrument of the invention. Like the previously described embodiments of the invention, the embodiment of FIGS. 14–17 is also comprised of a tubular rod 150 with opposite ends 152, 154 and a length of suture material 156 wrapped around one end. However, in this embodiment the rod is an inner rod 150 of a surgical instrument comprised primarily of a pair of concentric rods. In addition to the inner rod 150, the surgical instrument of FIGS. 14–17 also comprises an outer rod 158, an annular shoulder 162 with a sealing cap 164, a manual handle 166 and a spring 168. As with the previously described embodiments, the component parts of the embodiment shown in FIGS. 14–17 may be constructed of any materials acceptable for use in surgical instruments. Additionally, the dimensions of the component parts of the instrument shown in the drawing figures are chosen to better illustrate the component parts of the invention and are not to scale and should not be interpreted as limiting. The dimensions of the component parts of the embodiment shown in FIGS. 14–17 may be varied to best suit the embodiment of the surgical instrument of the invention shown in these drawing figures to any particular surgical operation.

Figures 14, 15:
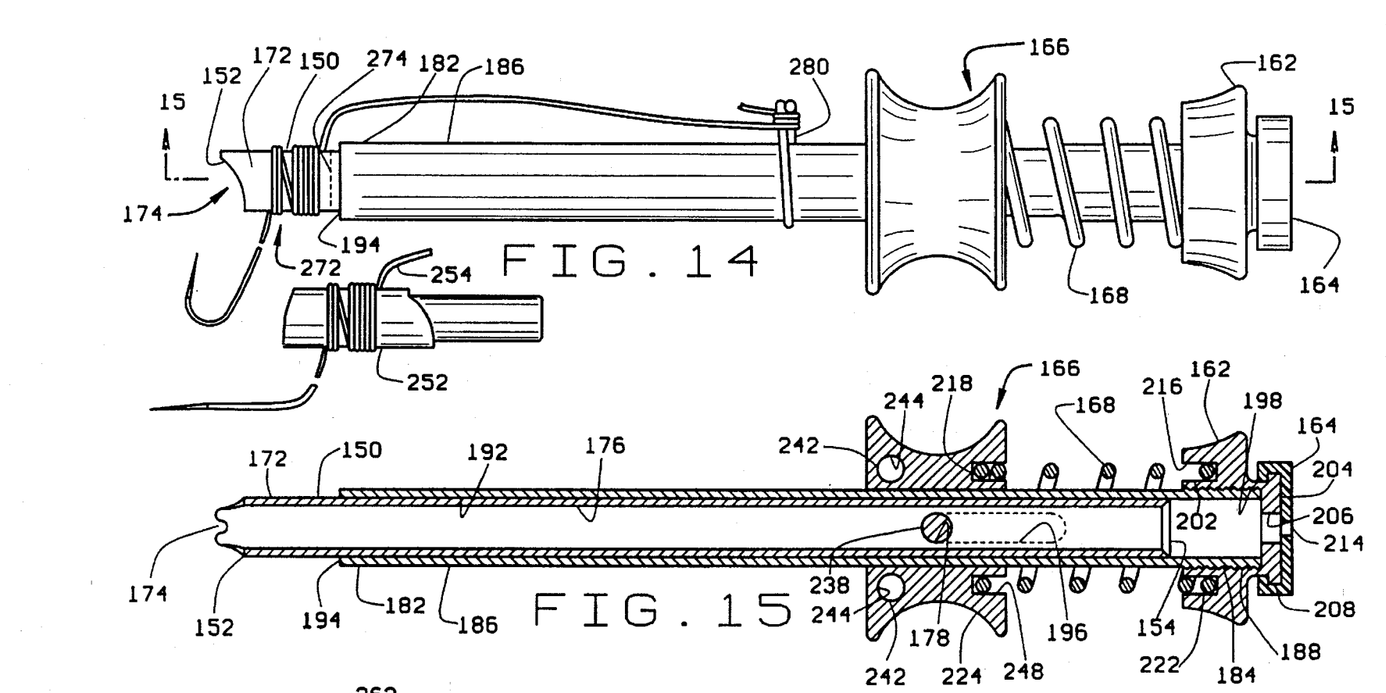
FIG. 14 shows a further embodiment of the surgical instrument of the invention.
FIG. 15 is a cross section of the instrument shown in FIG. 14 taken along the line 15—15 of FIG. 14.

First referring to the inner rod 150 of the instrument, the inner rod 150 has a longitudinal length with a first, distal end 152 and a second, proximal end 154. The inner rod is provided with a cylindrical exterior surface 172 that extends between the opposite distal and proximal ends. A portion of the rod distal end is formed as a two-pronged fork 174. The space between the prongs of the fork 174 is dimensioned large enough for a single strand of suture material to pass through the space but will prevent a knot in a strand of suture material from passing through the space. This dimensioning of the space between the fork prongs enables the fork to be used in manipulating a knot along a length of suture material. A longitudinal slot 175 is provided in the rod distal end opposite the fork 174. The slot 175 is employed in the same manner as the slots in the ends of the previously described embodiments. The inner rod 150 also has a cylindrical interior bore 176 that extends completely through the rod between its distal and proximal ends. A circular opening 178 extends through the inner rod 150 from the exterior surface 172 to the interior bore 176.

The length of suture material 156 extends from a proximal, free end of the suture along the length of the instrument and is wrapped in a desired pattern of loops on the distal end 152 of the inner rod. From the pattern of loops wrapped on the inner rod, the length of suture material then continues to its distal end, where it may be secured to a needle. The manner in which the length of suture material 156 is wrapped on the surgical instrument in preparation for use of the instrument will be described later in this specification.

The outer rod extends between a first, distal end 182 of the rod to a second, proximal end 184 of the rod. The outer rod 158 also has a cylindrical exterior surface 186 except for external screw threading 188 formed on the exterior surface adjacent the proximal end 184 of the rod. The outer rod 158 also has a cylindrical interior bore 192 extending completely through the rod between its distal and proximal ends. The interior diameter of the bore 192 generally matches the exterior diameter of the inner rod 150 enabling the inner rod 150 to be received in the interior bore 192 of the outer rod 158 for sliding, reciprocating movement therein. The longitudinal length of the outer rod 158 and its interior bore 192 is determined so that the entire longitudinal length of the inner rod 150, except for the fork 174 projecting from its distal end, can be completely received in the outer rod interior bore 192. At the outer rod distal end 182 the annular end face 194 of the rod surrounds the exterior surface of the inner rod 150 in close conformity. This enables the annular end face 194 to slide the loops of suture material 156 wrapped over the exterior surface of the inner rod over the inner rod exterior surface and off the distal end of the inner rod as the inner rod is reciprocated into the interior bore 192 of the outer rod. An elongated opening or slot 196 extends through the outer rod 158 from the exterior surface to the interior bore 192.

The annular shoulder 162 is screw threaded on the proximal end 184 of the outer rod 158. Alternatively, the shoulder could be silver soldered in place on the outer rod. The shoulder also has an interior bore 198 with internal screw threading 202 that is complementary to the external screw threading 188 of the outer rod distal end. An end wall 204 of the shoulder has a small diameter opening 206 extending therethrough communicating with the interior bores of the concentric rods 150, 158. A circular flange 208 surrounds the periphery of the end wall. An elastic sealing cap 164 is fitted over the circular flange 208 and covers over a portion of the end wall opening 206. The sealing cap 164 has a center opening 214 that communicates with the end wall opening 206 but is smaller in diameter and area than the end wall opening 206. At the opposite end of the shoulder 162 an annular groove 216 is formed completely surrounding the exterior surface of the outer rod 158.

The coiled spring 168 is received over the exterior surface of the outer rod 158. The spring has opposite distal 218 and proximal 222 ends and the proximal end of the spring is nested in the annular groove 216 of the shoulder 162.

The handle 166 is mounted on the exterior surface of the outer rod 158 for sliding, reciprocating movement thereon. The peripheral surface 224 of the handle is given a general concave configuration that enables the handle to be gripped easily between adjacent fingers of a surgeon's hand. To facilitate assembly of the handle onto the outer rod 158, the handle is formed in two halves 228, 232 best seen in FIG. 3. The two handle halves are formed with flat mating surfaces 234 with semicircular recesses 236 extending through the middle of the flat mating surfaces. The curvature of the semicircular recesses 236 conforms to the cylindrical exterior surface of the outer rod 158 enabling the two handle halves to come together and easily slide over the exterior surface of the outer rod. A cylindrical pin 238 extends from the semicircular recessed surface 236 of one of the handle halves. The length and diameter of the pin 238 is determined so that it will extend through the elongated slot 196 in the side of the outer rod 158 and into the circular opening 178 in the side of the inner rod 150, thereby connecting the handle half to the inner rod. The flat surface 234 of one of the handle halves 228 has an additional pair of projecting pins 242 thereon. The flat surface of the mating handle half 232 has a pair of holes 244 recessed therein dimensioned to receive the pair of pins 242 of the other handle half in assembling the two handle halves together over the exterior surface of the outer rod. End faces of the handle halves 228, 232 that face the annular shoulder 162 when assembled over the outer rod 158 have semicircular grooves 246, 248 formed therein that together form a circular groove in the handle end face when the two handle halves are assembled together. The circular groove formed is dimensioned to receive the distal end 218 of the coiled spring therein.

The component parts of the surgical instrument of the invention are easily assembled together and disassembled after use to enable sterilization of each of the parts. In assembling the component parts together, the inner rod 150 is first inserted into the interior bore 192 of the outer rod and is positioned so that the hole 178 in the side of the inner rod corresponds to the elongated slot 196 in the side of the outer rod. Next, the two handle halves 228, 232 are assembled over the exterior surface of the outer rod 158 so that the projecting pin 238 on the semicircular recess of the one handle half extends through the elongated slot 196 of the outer rod and into the opening 178 of the inner rod. The length of the projecting pin 238 is determined so that it is sufficiently long to extend through the elongated slot 196 of the outer rod and into the opposed hole 178 of the inner rod without extending into the interior bore of the inner rod. In this manner, the pin 238 does not obstruct the interior bore of the inner rod. In assembling the two handle halves together, the pair of pins 242 on the flat surface of the one handle half 228 are inserted into the pair of holes 244 in the other handle half 232. The handle halves are assembled together so that the semicircular grooves 246, 248 in their end faces face toward the proximal ends of the outer and inner rods.

Next, the distal end 218 of the coiled spring is inserted into the semicircular grooves 246, 248 formed in the handle halves and thereby secures the two handle halves together in their assembled condition around the exterior surface of the outer rod. The annular shoulder 162 is then screw threaded onto the screw threading 188 of the outer rod. As the annular shoulder 162 is screw threaded onto the outer rod, the coiled spring proximal end 222 is inserted into the annular groove 216 of the shoulder. When the annular shoulder 162 is threaded to its furthest extent onto the distal end of the outer rod 158, the coiled spring 168 will be slightly compressed.

When the shoulder 162 is soldered in place on the outer rod the spring is first assembled on the outer rod and compressed. Then the handle halves are assembled on the outer rod and the spring released, holding the handle halves in place.

From the above described assembly of the instrument it should be apparent that the slightly compressed spring 168 will bias the handle 166 away from the annular shoulder 162. By the connection of the handle to the inner rod 150 through the pins 238, the coiled spring 168 will also bias the inner rod 150 to its extended position relative to the outer rod 158 exposing a portion of its exterior surface adjacent the distal end 152 of the inner rod.

In use of the instrument of the invention, the length of suture material 156 having the needle secured at its distal end and a free proximal end is first wrapped in a desired pattern of loops on the inner rod exterior surface 172 projecting from the outer rod distal end 182. The free or proximal end of the length of suture is held at the proximal end of the instrument, or the right hand end as viewed in drawing FIGS. 1 and 2, either by the surgeon's hand or by a clamp on the exterior surface of the outer rod 158 which will be described later. The length of suture material is then extended longitudinally from its proximal end toward the exterior surface 172 of the inner rod distal end projecting from the distal end of the outer rod. On this exposed portion of the inner rod exterior surface, the length of suture material 156 is wrapped in a desired pattern of loops. The pattern of loops can be that described earlier with reference to other embodiments of the invention, or can be any pattern of loops that will produce a knot in the suture material when the suture loops are displaced off the distal end 152 of the inner rod and the needle at the distal end of the suture material is inserted through the center of the pattern of loops and is pulled tight. For example, the pattern of suture loops wrapped on the inner rod distal end can be that of a surgeon's knot, a Roeder's knot, a modified Roeder's knot, or any other pattern of suture loops that will form a knot that will slide over the portion of the length of suture connected to the needle when the needle is inserted through the centers of the loops as the loops are pushed off of the inner rod distal end onto the needle and attached portion of suture. After forming the desired pattern of suture loops on the inner rod distal end 152, the length of suture material then extends to the needle at its distal end. This excess length of suture material is needed to enable manipulation of the needle by the surgeon in making a stitch through body tissue with the needle. This excess length of suture material can be wrapped spirally on the inner rod distal end adjacent the pattern of loops formed on the inner rod in order to take up the slack in the suture material. The needle may then be inserted into the interior bore of the inner rod 150 and held by a surgical grasper (not shown) adjacent the inner rod distal end as the surgical instrument, with the grasper in its interior, is inserted through a trocar to a desired position in the body cavity.

With the instrument inserted into the body cavity so that the distal ends of the inner 150 and outer 158 rods are positioned proximate to the site in which a stitch is to be made, the grasper inserted through the interiors of the inner and outer rods may then be used to manipulate the needle at the end of the length of suture out of the interior bore of the inner rod 150. The same grasper inserted through the interiors of the inner and outer rods may be used to make the stitch in the body tissue. The grasper then regrips the needle at the opposite side of the stitch and returns the needle to the interior bore of the inner rod 150, pulling the length of suture wrapped spirally on the distal end of the inner rod from the rod end and through the stitch and back into the interior bore of the inner rod 150. As the needle and attached length of suture are pulled back into the interior bore of the inner rod 150, the length of suture is threaded through the pattern of loops formed on the exterior surface 172 of the inner rod distal end. With the length of suture passed through the stitch being pulled taut and with the distal end of the inner rod 150 positioned proximate to the site of the stitch, the handle 166 is then manually retracted toward the annular shoulder 162 against the bias of the spring 168 causing the annular end face 194 of the outer rod to push the pattern of loops formed in the length of suture off of the inner rod exterior surface 172 and over the length of suture connected to the needle. With the pattern of loops pushed off the distal end of the inner rod 150, the loops are snugged up about the suture and slid toward the stitch. The fork 174 formed at the distal end of the inner rod may be used to manipulate the pattern of loops toward the site of the stitch in the body tissue. The portion of suture material connected to the needle is further tightened by retracting the grasper through the interior of the inner rod 150 toward the proximal end of the instrument. The proximal end of the suture material held by the surgeon's hand or by the clamp at the proximal end of the instrument is also tightened, causing the pattern of loops formed in the suture material to constrict into a knot formed in the suture material at the site of the stitch. In the case of a surgeon's knot, each throw is slid to the site of the stitch and tightened before introducing another throw to the knot. With the knot tightened at the site of the stitch, the two portions of suture material leading from the stitch may then be cut free at the knot and removed from the site of the stitch formed. The instrument may then be reloaded with a length of suture wrapped in the desired pattern of loops on the inner rod distal end to form the next stitch in the body tissue.

Figure 17:
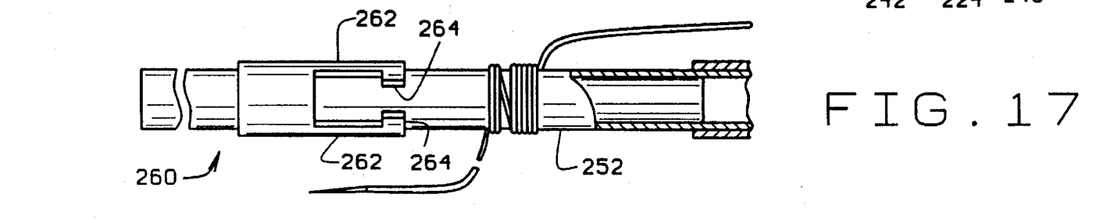
FIG. 17 shows a cartridge of the invention positioned on the end of the instrument of FIG. 14.

To assist in reloading suture material wrapped in a desired pattern of loops onto the distal end of the inner rod 150, the surgical instrument of the invention also includes a cartridge 252 that is partially shown in FIGS. 14 and 17. The cartridge is basically a cylindrical tube having an exterior surface with a cylindrical configuration and exterior diameter substantially identical to that of the inner rod 150. The cartridge 252 has a length of suture material wrapped in the desired pattern of loops over its exterior surface. The length of suture material 254 is wrapped around the exterior diameter in reverse order so that it can be slipped off the exterior surface of the cartridge 252 and onto the exterior surface 172 of the inner rod adjacent its distal end 152 and be in the proper orientation for use. In this manner the cartridge 252 enables the surgeon to quickly reload the instrument with a length of suture wrapped in the desired pattern of loops on the inner rod distal end 152 in preparation for making the next stitch with the instrument.

In order to facilitate transfer of the loops from the cartridge 252 to the exterior surface 172 of the inner rod, a pair of slidable tongs 260 may be provided. The tongs 260 are in the form of a cylinder having two tines extending along the cartridge 252. Each tine 262 has a T-shaped head 264 which may be used to grip an individual set of loops. Once the loops are gripped, the tongs 260 may be slid along the exterior surface of the cartridge 252 toward the inner rod to thereby transfer the loops from the cartridge to the distal end 152 of the inner rod. The tongs are made of a suitably resilient material such that when the tines are released, the T-shaped heads return to their original position and the tongs may be retracted onto the cartridge. In the preferred embodiment, the inner diameter of the tongs is large enough to permit loops of suture wound about the exterior surface of the cartridge to pass through the interior of the tongs. Thus, several sets of loops may be preloaded onto the cartridge and the tongs may be used to individually dispense one set of loops at a time without disturbing the other preloaded sets. Alternatively, some means of spring ejection may be employed to facilitate loading the loops onto the distal end 152 of the inner rod.

An alternative to the cartridge 252 described above is a detachable segment 272 of the inner rod distal end. The detachable segment is represented by the dashed lines 274 shown in FIG. 14. The detachable segment 272 of the inner rod may be screw threaded to the distal end of the rod to enable its quick replacement. The detachable segment 272 has the length of suture wrapped in the desired pattern of loops thereon when it is attached to the distal end of the inner rod 150. After the pattern of loops of suture material have been dispensed from the segment by operation of the instrument as described above, the instrument can be quickly reloaded with another length of suture wrapped in the desired pattern of loops by removing the spent segment 272 from the end of the inner rod and replacing it with a like segment having the desired pattern of loops of suture material wrapped thereon. With the instrument quickly reloaded in this manner, it is then again ready for use in forming a stitch in body tissue at a remote location in the same manner as described above.

Figure 16:
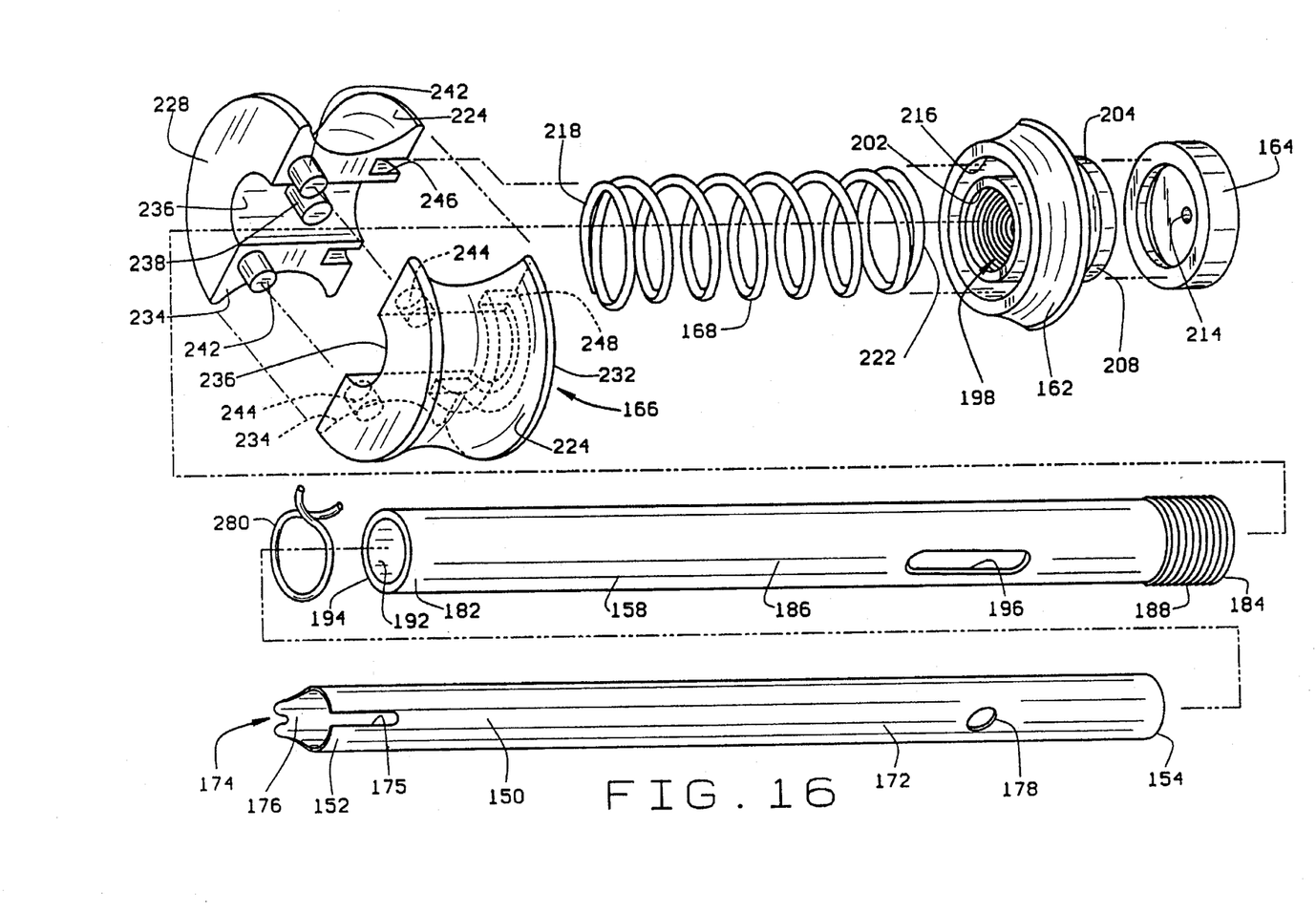
FIG. 16 shows an instrument of FIG. 14 disassembled.

A typical wire hose clamp 280 may be clamped over the cylindrical exterior surface 186 of the outer rod 158 as shown in FIGS. 14 and 16. Wrapping the suture around the horns of the hose clamp two or three times grips the free end of the suture sufficiently to prevent it from being separated from the hose clamp. Thus, the free end of the suture may be attached to the instrument until ready for manipulation. Alternate clamps and other attachment means are also within the scope of this invention.

Figure 18:
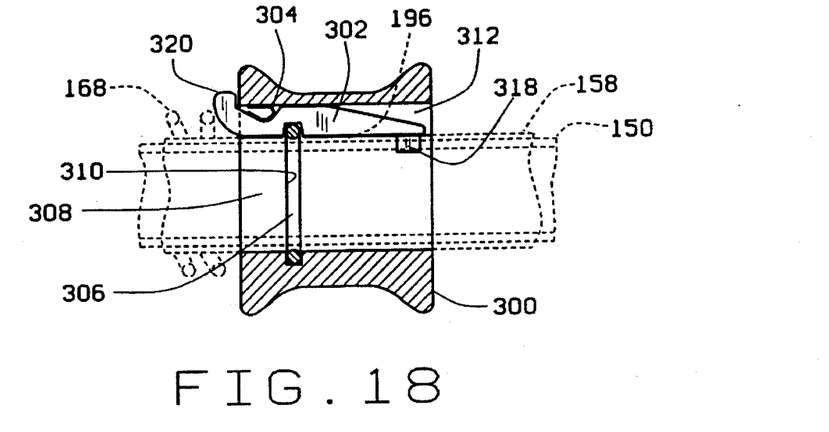
FIGS. 18–21 show variant embodiments of the instrument handle.
Figure 19:
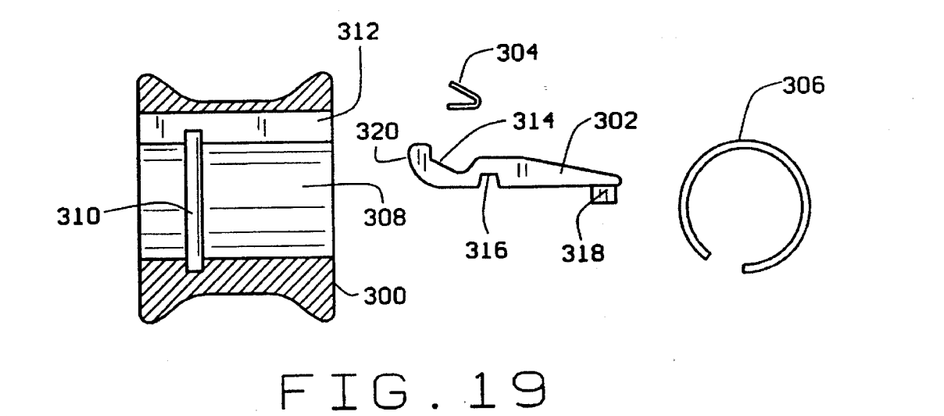

FIGS. 18–21 show variant embodiments of the handle of the surgical instrument of the invention. FIGS. 18 and 19 disclose a first embodiment of these handle variants with the handle shown assembled to the concentric tubular rods in FIG. 18 and shown disassembled into its component parts in FIG. 19.

The handle embodiment of FIGS. 18 and 19 is comprised of a cylindrical handle member 300, a locking lever 302, a leaf spring 304 and a circular spring 306.

The handle member 300 is very similar to the handle of the previously described embodiment of the instrument except that it is provided as a single cylindrical member instead of two half members. The exterior configuration of the handle member is substantially identical to that of the handle of the previously described embodiment. A cylindrical bore 310 extends through the center of the handle member 300. The bore has an interior diameter that is matched to the exterior diameter of the outer rod so that the handle member 300 may be mounted for sliding reciprocating movement over the exterior of the concentric rods as is shown in FIG. 18 where the concentric rods are represented in phantom lines. An annular groove 310 extends completely around the interior bore 308 of the handle member. An axial slot 312 is formed in the interior bore 308 extending the axial length of the bore.

The locking lever 302 has a width dimension determined to enable the locking lever to be inserted into the axial slot 312 of the handle member in the position shown in FIG. 18. A recess 314 is provided in the top of the locking lever 302 and the leaf spring 304 is received in the recess as the locking lever 302 is positioned in the axial slot 312. To hold the locking lever and leaf spring in their relative positions in the slot 312 shown in FIG. 18, a notch 316 is provided in the bottom of the locking lever 302 opposite the leaf spring recess 314. The circular spring 306 is compressed and inserted into the handle member interior bore 308 where it is positioned in the annular groove 310 and the lever notch 316. The resiliency of the circular spring 306 holds the locking lever 302 in the axial slot 312 of the handle member.

With the component parts of the handle assembled together and prior to their positioning on the exterior of the outer rod of the instrument, the leaf spring 304 pivots the locking lever 302 in the axial slot 312 and about the circular spring 306 so that a pin 318 of the lever 302 is retracted into the axial slot 312 of the handle member. With the pin 318 in the axial slot, the assembled component parts of the handle can be easily slipped over the exterior surface of the outer rod of the instrument. The end 320 of the locking lever that projects from the handle member axial slot 312 is moved radially outwardly relative to the handle member 300 to cause the lever pin 318 to engage through the elongated slot 196 of the outer rod member and into the circular opening 178 of the inner rod member, thereby connecting the handle member 300 to the inner rod member. The coil spring 168 of the instrument engages against the locking lever end 320 and maintains the locking lever in the position shown in FIG. 18 with the lever pin 318 inserted through the slot 196 of the outer rod member and into the opening 178 of the inner rod member.

Figure 20:
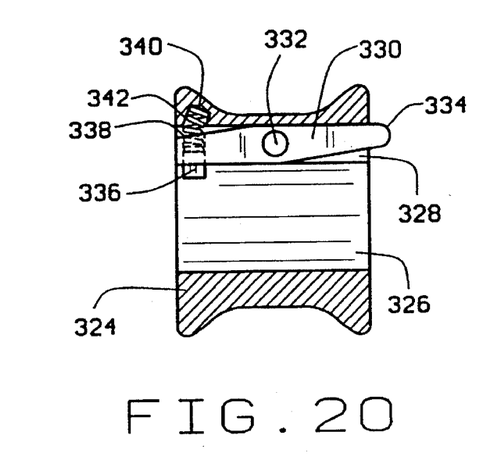

A further embodiment of the handle member 324 is shown in FIG. 20. This embodiment is similar to the embodiment of FIGS. 18 and 19 in that it is basically comprised of a cylindrical one piece handle member 324 with a cylindrical interior bore 326 extending through its center and an axial slot 328 extending along one side of the interior bore. A locking lever 330 is positioned in the axial slot 328 and a pivot pin 332 is inserted into the handle member and the locking lever to mount the locking lever in the axial slot 328 for pivoting movement of the lever about the pin. An end 334 of the lever projects from the handle axial slot 328 and a lever pin 336 projects from the opposite end of the lever. The lever pin 336 projects through the elongated slot 196 of the outer rod and into the circular opening 178 of the inner rod (not shown in FIG. 20) in connecting the handle to the inner rod. This connection is much the same as the handle embodiment of FIGS. 18 and 19. A spring hole 338 is formed in the top of the lever 330 opposite the lever pin 336 and a corresponding spring hole 340 is formed in the handle member 324 at the top of the axial slot 328. A small coil spring 342 is inserted into the lever hole 338 and the handle hole 340 biasing the locking lever 330 to the position shown in FIG. 20 where the lever pin 336 extends through the outer rod slot 196 and into the inner rod circular opening 178 connecting the handle member 324 to the inner rod.

The handle embodiment of FIG. 20 is assembled onto the outer rod of the instrument by depressing the projecting end 334 of the lever thus raising the lever pin 336 into the axial slot 328. The handle member 324 is then slipped over the exterior surface of the outer rod until it is properly positioned over the outer rod slot 196 and the inner rod circular opening 178. The end 334 of the locking lever is then released, causing the coil spring 342 to push downward on the locking lever and thereby causing the lever pin 336 to be inserted through the outer rod slot 196 and into the inner rod circular opening 178 connecting the handle member to the inner rod.

Figure 21:
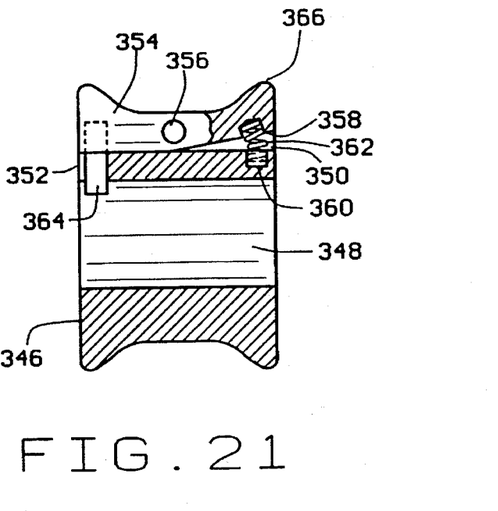

A still further embodiment of the handle is shown in FIG. 21. The FIG. 21 embodiment is also comprised of a single piece, cylindrical handle member 346 as were the previous embodiments of FIGS. 18–20. The handle member 346 has a cylindrical interior bore 348 extending through its center. However, unlike the previously described embodiments of the handle member, the FIG. 21 embodiment has an axial slot 350 extending into the handle member from its exterior surface. A notch 352 also extends from the axial slot 350 through to the handle member interior bore 348.

A locking lever 354 is positioned in the axial slot 350 and held in place by a pivot pin 356. As seen in the drawing figure, a portion of the bottom surface of the locking lever 354 is cut away so that the locking lever bottom surface tapers away from the bottom of the handle member axial slot 350. This enables the locking lever to pivot in the axial slot about the pivot pin 356. A spring hole 358 is formed in the tapered bottom surface of the locking lever 354 and a second spring hole 360 is formed in the bottom of the handle member axial slot 350 opposite the locking lever spring hole. A small coil spring 362 is assembled into the spring holes of the locking lever and the handle member. The coil spring biases the locking member to its position relative to the handle member shown in FIG. 21. The opposite end of the locking lever 354 has a lever pin 364 extending downwardly therefrom. The lever pin 364 extends through the notch 352 of the handle member and into the handle member interior bore 348 where it extends through the elongated slot 196 of the outer rod member and into the circular opening 178 of the inner rod member, thereby connecting the handle member 346 to the inner rod.

In mounting the embodiment of the handle shown in FIG. 21 on the exterior surface of the instrument outer rod, the end of the locking lever 366 is first depressed against the bias of the coil spring 362 causing the lever to pivot about the pivot pin 356 and retracting the lever pin 364 from the interior bore 348 and into the notch 352. The handle member 346 is then slipped over the exterior surface of the instrument outer rod until it is positioned over the outer rod elongated slot 196 and the inner rod circular opening 178. The lever end 366 is then released causing the coil spring 362 to pivot the locking lever about the pivot pin 356 and causing the lever pin 364 to be inserted through the elongated slot 196 of the outer rod and into the circular opening 178 of the inner rod, thereby connecting the handle member to the inner rod.

While the present invention has been described by reference to a specific embodiment, it should be understood that modifications and variations of the invention may be constructed without departing from the scope of the invention defined in the following claims.

What is claimed is:

1. A surgical instrument for tying a knot in a length of suture, the instrument comprising:

an outer rod having a longitudinal length with opposite distal and proximal ends, the outer rod having a hollow interior bore extending therethrough;

a sealing cap attached to the outer rod proximal end providing a seal over the interior bore at the outer rod proximal end;

an inner rod having a longitudinal length with opposite distal and proximal ends, the inner rod being received in the interior bore of the outer rod for reciprocating movement therein between an extended position of the inner rod relative to the outer rod and the sealing cap where a portion of the inner rod adjacent the inner rod distal end projects from the outer rod interior bore at the outer rod distal end and the inner rod proximal end is positioned in the outer rod interior bore, and a retracted position of the inner rod relative to the outer rod and the sealing car where the portion of the inner rod is at least partially retracted into the outer rod interior bore and the inner rod proximal end is positioned in the outer rod interior bore; and an exterior surface on one of the inner and outer rods providing a surface for a length of suture to be wrapped in a pattern of loops thereon, the exterior surface providing a surface which maintains the length of suture in the pattern of wrapped loops as the pattern of loops is slipped over and off from the surface in response to relative movement between the inner rod and the outer rod.

2. The instrument of claim 1, wherein:

the exterior surface is on the portion of the inner rod, the pattern of loops is capable of being wrapped on the exterior surface with the inner rod in the extended position relative to the outer rod, and the pattern of loops is slipped over and off the exterior surface by the outer rod distal end in response to the inner rod moving from the extended position to the retracted position.

3. The instrument of claim 2, further comprising:

a cartridge having an exterior surface, the cartridge exterior surface having a length of suture wrapped in a pattern of loops thereon and the cartridge exterior surface having a configuration that is complementary to the inner rod exterior surface thereby enabling the pattern of suture loops wrapped on the cartridge exterior surface to be slipped off the cartridge and onto the portion of the inner rod exterior surface.

4. The instrument of claim 1, further comprising:

means connected to the outer rod and the inner rod for biasing the inner rod toward the extended position of the inner rod relative to the outer rod, the means for biasing the inner rod maintaining a biasing force on the inner rod while the inner rod is moved between the extended and retracted positions.

5. The instrument of claim 4, wherein:

the means for biasing the inner rod includes a spring with opposite first and second ends where the first end of the spring acts on the inner rod and the second end of the spring acts on the outer rod.

6. The instrument of claim 4, wherein:

the outer rod has an exterior surface and an opening is provided in the outer rod extending from the outer rod exterior surface to the outer rod interior bore; and a handle is mounted on the outer rod exterior surface for movement relative thereto, the handle extending through the opening in the outer rod to the inner rod received in the outer rod interior bore and being connected to the inner rod.

7. The instrument of claim 6, wherein:

the handle includes a lever mounted on the handle for movement of the lever relative to the handle between first and second positions, and the lever is configured so that it extends through the opening in the outer rod and connects with the inner rod when in the first position and so that the lever is retracted out of the opening in the outer rod disconnecting the handle from the inner rod when the lever is in the second position.

8. The instrument of claim 6, wherein:

the inner rod exterior surface has a portion that covers over and closes the opening in the outer rod exterior surface from the outer rod interior bore as the inner rod is reciprocated between the extended position and the retracted position of the inner rod relative to the outer rod.

9. The instrument of claim 1, wherein:

a segment of the inner rod distal end is detachable from the inner rod; and a like segment of the inner rod distal end having a length of suture wrapped in a pattern of loops thereon is attachable to the inner rod to replace the detached segment of the inner rod distal end.

10. The instrument of claim 1, wherein:

the interior bore of the outer rod extends completely through the outer rod and the inner rod has an interior bore that extends completely therethrough, whereby a second surgical instrument can be inserted completely through the interior bores of the outer rod and inner rod.

11. The instrument of claim 1, wherein:

the sealing cap has an opening therethrough that is dimensioned sufficiently large as to permit insertion of a separate surgical instrument through the sealing cap opening while sealing around the instrument.

12. The instrument of claim 11, wherein:

the sealing cap is constructed of an elastic material that enables the sealing cap opening to stretch to accommodate insertion of the separate surgical instrument through the sealing cap opening while sealing around the instrument.

13. A surgical instrument for tying a knot in a length of suture, the instrument comprising:

an outer tubular rod having a longitudinal length with opposite distal and proximal ends and a hollow interior bore extending completely therethrough;

a sealing cap attached to the outer rod proximal end and covering over the interior bore at the outer rod proximal end;

an inner tubular rod having a longitudinal length with opposite distal and proximal ends and a hollow interior bore extending completely therethrough, the inner rod is received in the interior bore of the outer rod for reciprocating movement therein between an extended position of the inner rod relative to the outer rod and the sealing cap where a portion of an exterior surface of the inner rod adjacent the inner rod distal end projects from the outer rod interior bore at the outer rod distal end and the inner rod proximal end is positioned in the outer rod interior bore, and a retracted position of the inner rod relative to the outer rod where the portion of the inner rod exterior surface is at least partially retracted into the outer rod interior bore and the inner rod proximal end is positioned in the outer rod interior bore, the portion of the inner rod exterior surface providing a surface for a length of suture to be wrapped in a pattern of loops thereon with the inner rod in the extended position relative to the outer rod, and the portion of the inner rod exterior surface providing a surface which maintains the length of suture in the pattern of wrapped loops as the pattern of loops is slipped over the exterior surface and off the inner rod distal end by the outer rod distal end in response to the inner rod moving from the extended position to the retracted position.

14. The instrument of claim 13, wherein:

the hollow interior bores of the outer and inner rods are dimensioned sufficiently large to enable another surgical instrument to be inserted through the interior bores of the outer and inner rods.

15. The instrument of claim 13, further comprising:

a cartridge separate from the outer and inner rods and having a cylindrical exterior surface conforming to the portion of the inner rod exterior surface, the cartridge exterior surface having a length of suture wrapped in a pattern of loops thereon and the exterior surface of the cartridge enabling the cartridge to be positioned against the distal end of the inner rod in the extended position of the inner rod and enabling the pattern of suture loops wrapped on the cartridge exterior surface to be slipped off the cartridge and onto the inner rod exterior surface.

16. The instrument of claim 13, wherein:

the outer rod has an exterior surface and an opening is provided in the outer rod that extends from the outer rod exterior surface through to the interior bore of the outer rod; and a handle is mounted on the exterior surface of the outer rod for movement of the handle relative thereto, the handle extends through the opening in the outer rod and is connected to the inner rod in the outer rod interior bore.

17. The instrument of claim 16, wherein:

the handle includes a lever mounted on the handle for movement of the lever relative to the handle between first and second positions, and the lever is configured so that it extends through the opening in the outer rod and connects with the inner rod when in the first position and so that the lever is retracted out of the opening in the outer rod disconnecting the handle from the inner rod when the lever is in the second position.

18. The instrument of claim 16, wherein:

a shoulder is mounted on the exterior surface of the outer rod at the proximal end of the outer rod; and a spring is mounted between the handle and the shoulder and biases the handle away from the shoulder and thereby, through the connection of the handle to the inner rod, biases the inner rod to the extended position relative to the outer rod.

19. The instrument of claim 16, wherein:

the inner rod exterior surface has a portion that covers over and closes the opening in the outer rod exterior surface from the outer rod interior bore as the inner rod is reciprocated between the extended position and the retracted position of the inner rod relative to the outer rod.

20. The instrument of claim 13, wherein:

a segment of the inner rod distal end is detachable from the inner rod and replaceable by a like segment of the inner rod distal end having a length of suture wrapped in the pattern of loops thereon.

21. The instrument of claim 13, wherein:

the sealing cap has an opening therethrough that is dimensioned sufficiently large as to permit insertion of a separate surgical instrument through the sealing cap opening while sealing around the instrument.

22. A surgical instrument for tying a knot in a length of suture, the instrument comprising:

an outer rod having a longitudinal length with opposite distal and proximal ends and a hollow interior bore extending at least partially therethrough from the outer rod distal end, the outer rod having an exterior surface with an opening therein, the opening extending from the exterior surface through to the interior bore;

an inner rod having a longitudinal length with opposite distal and proximal ends, the inner rod is received in the interior bore of the outer rod for longitudinal reciprocating movement therein between an extended position of the inner rod relative to the outer rod where a portion of an exterior surface of the inner rod adjacent the inner rod distal end projects from the outer rod interior bore at the outer rod distal end, and a retracted position of the inner rod relative to the outer rod where the portion of the inner rod exterior surface is retracted into the outer rod interior bore, the portion of the inner rod exterior surface providing a surface for a length of suture to be wrapped in a pattern of loops thereon with the inner rod in the extended position relative to the outer rod, and the portion of the inner rod exterior surface providing a surface which maintains the length of suture in the pattern of wrapped loops as the pattern of loops is slipped over the exterior surface and off the inner rod distal end by the outer rod distal end in response to the inner rod moving from the extended position to the retracted position, the inner rod exterior surface having a second portion that covers over and closes the opening in the outer rod exterior surface from the outer rod interior bore as the inner rod is reciprocated between the extended position and the retracted position of the inner rod relative to the outer rod; and a handle mounted on the exterior surface of the outer rod for longitudinal sliding movement of the handle relative to the outer rod, the handle extending through the opening in the outer rod and being connected to the inner rod in the interior bore of the outer rod whereby longitudinal reciprocating sliding movement of the handle on the outer rod imparts longitudinal reciprocating movement to the inner rod in the outer rod interior bore.

23. The instrument of claim 22, wherein:

the handle includes a lever mounted on the handle for movement of the lever relative to the handle between first and second positions, and the lever is configured so that it extends through the opening in the outer rod and connects with the inner rod when in the first position and so that the lever is retracted out of the opening in the outer rod disconnecting the handle from the inner rod when the lever is in the second position.

24. The instrument of claim 22, wherein:

the handle is mounted on the outer rod in a position intermediate the distal and proximal ends of the outer rod and a shoulder is affixed to the outer rod proximal end, a spring is mounted between the shoulder and the handle and biases the handle longitudinally away from the shoulder and thereby, through the connection between the handle and the inner rod, biases the inner rod to the extended position relative to the outer rod.

25. The instrument of claim 22, further comprising:

a cartridge separate from the outer and inner rods and having a cylindrical exterior surface conforming to the portion of the inner rod exterior surface, the cartridge exterior surface having a length of suture wrapped in a pattern of loops thereon and the exterior surface of the cartridge enabling the cartridge to be positioned against the distal end of the inner rod in the extended position of the inner rod and enabling the pattern of suture loops wrapped on the cartridge exterior surface to be slipped off the cartridge and onto the inner rod exterior surface.

26. The instrument of claim 22, wherein:

a segment of the inner rod having the portion of the inner rod exterior surface thereon is detachable from the inner rod and replaceable by a like segment of the inner rod having a length of suture wrapped in the pattern of loops on the like segment.

27. The instrument of claim 22, wherein:

a sealing cap is attached to the outer rod proximal end and provides a seal over the interior bore of the outer rod at the outer rod proximal end, and the sealing cap has an opening therethrough that is dimensioned sufficiently large as to permit insertion of a separate surgical instrument through the sealing cap opening while sealing around the instrument.

* * * * *